United States Patent
Slany et al.

(10) Patent No.: US 6,906,222 B2
(45) Date of Patent: Jun. 14, 2005

(54) PREPARATION FOR PRODUCTION OF FORMIC ACID FORMATES

(75) Inventors: Michael Slany, Kirchheim (DE); Martin Schäfer, Grünstadt (DE); Jörn Karl, Mannheim (DE); Michael Röper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/494,701

(22) PCT Filed: Oct. 29, 2002

(86) PCT No.: PCT/EP02/12046

§ 371 (c)(1),
(2), (4) Date: May 6, 2004

(87) PCT Pub. No.: WO03/040078

PCT Pub. Date: May 15, 2003

(65) Prior Publication Data

US 2005/0010067 A1 Jan. 13, 2005

(30) Foreign Application Priority Data

Nov. 9, 2001 (DE) .......................................... 101 54 715
Mar. 12, 2002 (DE) .......................................... 102 10 730

(51) Int. Cl.$^7$ .............................................. C07C 53/06
(52) U.S. Cl. ..................................................... 562/609
(58) Field of Search ......................................... 562/609

(56) References Cited

U.S. PATENT DOCUMENTS 4,218,568 A    8/1980  Hohenschutz et al.
4,261,755 A    4/1981  Berry et al.
6,137,005 A  * 10/2000  Hornevik .................... 562/609

FOREIGN PATENT DOCUMENTS

| DE | 424 017 | 1/1926 |
| GB | 1 505 388 | 3/1978 |
| WO | 96/35657 | 11/1996 |
| WO | 97/05783 | 2/1997 |
| WO | 98/02911 | 5/1998 |
| WO | 99/12435 | 3/1999 |
| WO | 00/08929 | 2/2000 |
| WO | 01/19207 | 3/2001 |

OTHER PUBLICATIONS

Gmelins Handbuch der anorganischen Chemie, 8$^{th}$ Ed., No. 21, pp. 816 to 819, 1928.

Gmelins Handbuch der anorganischen Chemie, 85$^{th}$ Ed., No. 22, pp. 912 to 921, 1936.

Kendall et l., Journal of the American Chemical Soc., vol. 43, 1921, pp. 1470 to 1481.

* cited by examiner

*Primary Examiner*—Paul A. Zucker
(74) *Attorney, Agent, or Firm*—Novak Druce & Quigg, LLP

(57) ABSTRACT

A process is described for preparing acid formates in which methyl formate is reacted with water and a basic compound having a $pK_a$ of the conjugate acid of the corresponding dissociation state of ≧3 measured at 25° C. in aqueous solution, the methanol formed is separated off and, optionally, the desired acid content is set by adding formic acid.

8 Claims, No Drawings

PREPARATION FOR PRODUCTION OF FORMIC ACID FORMATES

The present invention relates to a process for preparing acid formates.

Acid formates have an antimicrobial activity and are used, for example, for preserving and acidifying materials of vegetable and animal origin, for example grasses, agricultural products or meat, for treating biowastes, or as an additive for animal nutrition.

Acid formates and preparation methods for these have long been known, thus, Gmelins Handbuch der anorganischen Chemie [Gmelin's Handbook of Inorganic Chemistry], 8th edition, Number 21, pages 816 to 819, Verlag Chemie GmbH, Berlin 1928 and Number 22, pages 919 to 921, Verlag Chemie GmbH, Berlin 1937, describes the synthesis of sodium diformate or potassium diformate by dissolving sodium formate or potassium formate in formic acid. The crystalline diformates may be obtained by lowering the temperature and evaporating off excess formic acid.

DE 424017 teaches the preparation of sodium acid formates having varying acid content by introducing sodium formate into aqueous formic acid in an appropriate molar ratio. By cooling the solution the corresponding crystals are obtained.

According to J. Kendall et al., Journal of the American Chemical Society, Vol. 43, 1921, pages 1470 to 1481, potassium acid formates are obtainable by dissolving potassium carbonate in 90% strength formic acid, forming carbon dioxide. The corresponding solids can be obtained by crystallization.

GB 1,505,388 discloses the preparation of acid carboxylate solutions by mixing the carboxylic acid with a basic compound of the desired cation in aqueous solution. Thus, for example, in the preparation of acid ammonium carboxylate solutions, ammonia water is used as basic compound.

U.S. Pat. No. 4,261,755 describes the preparation of acid formates by reacting an excess of formic acid with the hydroxide, carbonate or bicarbonate of the corresponding cation.

WO 96/35657 teaches the preparation of products which contain disalts of formic acid by mixing potassium, sodium, cesium or ammonium formate, potassium, sodium or cesium hydroxide, carbonate or bicarbonate, or ammonia with optionally aqueous formic acid, subsequently cooling the reaction mixture, filtering the resultant suspension and drying the resultant filter cake and recirculating the filtrate.

A disadvantage of the abovementioned processes is that for each mole of formate formed by reaction with the basic compounds, one mole of formic acid is consumed and, as a result, based on the entire added-value chain, the processes are complex, costly and energy consuming.

It is an object of the present invention, therefore, to provide a process which no longer has the abovementioned disadvantages, which makes it possible to prepare acid formates on an industrial scale in high yield, with simultaneous high flexibility with respect to composition and using readily accessible raw materials and permits simple process design with low capital costs.

We have found that this object is achieved by a process for preparing acid formates which comprises reacting methyl formate with water and a basic compound having a $pK_a$ of the conjugate acid of the corresponding dissociation state of $\geq 3$ measured at 25° C. in aqueous solution, separating off the methanol formed and, optionally, setting the desired acid content by adding formic acid.

Acid formates are compounds and mixtures which contain formate anions (HCOO—), cations ($M^{x+}$) and formic acid (HCOOH). They can be present together in the form of a solid or a liquid and may contain other components, for example other salts, additives or solvents, for example water. Generally, the acid formates can be represented by the formula $$\text{HCOO}-M^{x+}{}_{1/x} * y\text{HCOOH} \qquad (I),$$

where M is a monovalent or polyvalent inorganic or organic cation, x is a positive number and indicates the charge of the cation and y is the molar fraction of formic acid based on the formate anion. The molar fraction of formic acid based on the formate anion y is generally from 0.01 to 100, preferably from 0.05 to 20, particularly preferably from 0.5 to 5, and in particular from 0.9 to 3.1.

The nature of the inorganic or organic cation $M^{x+}$ is not critical in principle provided that it is stable under the conditions under which the acid formate is to be handled. This is also taken to mean, for example, stability toward the reducing formate anion. Possible inorganic cations are the monovalent and/or polyvalent metal cations of metals from groups 1 to 14 of the Periodic Table of the Elements, for example lithium ($Li^+$), sodium ($Na^+$), potassium ($K^+$), cesium ($Cs^+$), magnesium ($Mg^{2+}$), calcium ($Ca^{2+}$), strontium ($Sr^{2+}$) and barium ($Ba^{2+}$), preferably sodium ($Na^+$), potassium ($K^+$), cesium ($Cs^+$) and calcium ($Ca^{2+}$). Possible organic cations are unsubstituted ammonium ($NH_4^+$) and ammonium substituted by one or more carbon-containing radicals which can optionally also be bound to one another, for example methylammonium, dimethylammonium, trimethylammonium, ethylammonium, diethylammonium, triethylammonium, pyrollidinium, N-methylpyrroldinium, piperidinium, N-methylpiperidinium or pyridinium.

A carbon-containing organic radical is an unsubstituted or substituted aliphatic, aromatic or araliphatic radical having from 1 to 30 carbons. This radical can contain one or more heteroatoms, such as oxygen, nitrogen, sulfur or phosphorus, for example —O—, —S—, —NR—, —CO—, —N=, —PR— and/or —PR$_2$ and/or can be substituted by one or more functional groups which contain, for example, oxygen, nitrogen, sulfur and/or halogen, for example by fluorine, chlorine, bromine, iodine and/or a cyano group (the radical R in this case is also a carbon-containing organic radical). The carbon-containing organic radical can be a monovalent or polyvalent, for example divalent or trivalent, radical.

To prepare the acid formates, in the inventive process, methyl formate is reacted with water and a basic compound having a $PK_a$ of the conjugate acid in the corresponding dissociation state of $\geq 3$, preferably $\geq 3.5$, particularly preferably $\geq 9$ and very particularly preferably $\geq 10$, measured at 25° C. in aqueous solution. The basic compound can be inorganic or organic. The basic compound can be a salt or a covalent compound. The conjugate acid of the corresponding dissociation state in this case is the acid formed by formal addition of a proton ($H^+$).

In the event that the basic compound is a salt, this can in general be represented by the formula $$M^{x+}{}_a A^{a-}{}_x \qquad (II),$$

where M and x have the meaning specified under (I) and A is an inorganic or organic anion having the charge "a–". The conjugate acid of the corresponding dissociation state thus corresponds to $HA^{(a-1)-}$. The corresponding dissociation equation, which defines the $pK_a$ to be used, is as follows

 (III)

In the event that the basic compound is a covalent compound B, the dissociation equation which defines the $PK_a$ to be used is as follows

 (IV)

Examples of suitable basic compounds are the salts $M^{x+}{}_a A^{a-}{}_x$ (II), where $M^{x+}$ is a monovalent or polyvalent metal cation of a metal as described above and $A^{a-}$ is an anion as listed in Table 1a and the covalent compounds B listed in Table 1b.

TABLE 1a

Possible anions $A^{a-}$ of suitable basic compounds and $PK_aS$ (measured at 25° C. in aqueous solution) of the conjugate acids of the corresponding dissociation states.

| Anions $A^{a-}$ | Conjugate acid | $pK_a$ |
|---|---|---|
| Hydroxide ($OH^-$) | Water ($H_2O$) | 14.0 |
| Carbonate ($CO_3^{2-}$) | Hydrogen carbonate ($HCO_3^-$) | 10.3 |
| Hydrogen carbonate ($HCO_3^-$) | Carbonic acid ($H_2CO_3$) | 6.4 |
| Borate ($BO_3^{3-}$) | Hydrogen borate ($HBO_3^{2-}$) | >14 |
| Hydrogen borate ($HBO_3^{2-}$) | Dihydrogen borate ($H_2BO_3^-$) | >14 |
| Dihydrogen borate ($H_2BO_3^-$) | Boric acid ($H_3BO_3$) | 9.3 |
| Phosphate ($PO_4^{3-}$) | Hydrogen phosphate ($HPO_4^{2-}$) | 12.3 |
| Hydrogen phosphate ($HPO_4^{2-}$) | Dihydrogen phosphate ($H_2PO_4^-$) | 7.2 |
| Formate | Formic acid | 3.8 |
| Acetate | Acetic acid | 4.8 |
| Propionate | Propionic acid | 4.9 |
| Oxalate ($C_2O_4^{2-}$) | Hydrogen oxalate ($HC_2O_4^-$) | 4.2 |
| 2-Ethylhexanoate ($C_4H_9$—$CH(C_2H_5)$—$COO^-$) | 2-Ethylhexanoic acid ($C_4H_9$—$CH(C_2H_5)$—$COOH$) | >4 |

TABLE 1b

Possible covalent bases B as suitable basic compounds and $pK_aS$ (measured at 25° C. in aqueous solution) of the conjugate acids of the corresponding dissociation states.

| Covalent base B | Conjugate acid | $pK_a$ |
|---|---|---|
| Ammonia | Ammonium | 9.3 |
| Methylamine | Methylammonium | 10.6 |
| Dimethylamine | Dimethylammonium | 10.7 |
| Trimethylamine | Trimethylammonium | 9.8 |
| Ethylamine | Ethylammonium | 10.7 |
| Diethylamine | Diethylammonium | 11.0 |
| Triethylamine | Triethylammonium | 10.8 |
| Pyrollidine | Pyrollidinium | 11.3 |
| N-Methylpyrroldine | N-Methylpyrroldinium | 10.3 |
| Piperidine | Piperidinium | 11.1 |
| N-Methylpiperidine | N-Methylpiperidinium | 10.1 |
| Pyridine | Pyridinium | 5.3 |

Preferably, in the inventive process, the basic compound used is lithium hydroxide, lithium hydrogen carbonate, lithium carbonate, lithium formate, sodium hydroxide, sodium hydrogen carbonate, sodium carbonate, sodium formate, potassium hydroxide, potassium hydrogen carbonate, potassium carbonate, potassium formate, ammonium carbonate, ammonium hydrogen carbonate and/or ammonia, particularly preferably sodium hydroxide, sodium hydrogen carbonate, sodium carbonate, sodium formate, potassium hydroxide, potassium hydrogen carbonate, potassium carbonate, potassium formate and/or ammonia, and particularly preferably sodium hydroxide, sodium carbonate, sodium formate, potassium hydroxide, potassium carbonate and/or potassium formate, in particular sodium hydroxide, sodium formate, potassium hydroxide and/or potassium formate.

The manner in which the basic compounds are added is generally not critical in the inventive process. They can be added in solid, liquid or gaseous form, as pure substance, as mixture of substances or as solution. Examples which may be mentioned are addition in the form of aqueous solutions (for example aqueous solutions of the alkali metal salts or ammonia water), in the form of solid compounds (for example powders of the alkali metal salts), in the gaseous state (for example gaseous ammonia). Preference is given to addition in the form of their aqueous solutions.

The sequence in which the starting materials are added is also in general not critical in the inventive process. Thus, it is possible, for example, to introduce first the basic compound in solid or liquid form (for example as aqueous solution) and then to introduce the methyl formate in the liquid or gaseous state with stirring. It is also possible to introduce first the methyl formate in liquid form and then to add the basic compound. In addition, obviously, the starting materials can also be added in parallel in the desired ratio.

The molar ratio of methyl formate to the basic compound is generally not critical for the process. Generally, at least as much methyl formate is used with respect to the basic compound so that, on the basis of the reaction stoichiometry, all of said basic compound is converted into formate. The critical parameter of this is what is termed the molar equivalent of the basic compound, which must take into account in this case all dissociation states which lead by addition of protons to conjugate acids which have a $PK_a$ of $\geq 3$, measured at 25° C. in aqueous solution. Thus, for example, a methyl formate/potassium hydroxide molar ratio of 2.0 leads to the formation of potassium diformate HCOOK*HCOOH, since 1 mol of KOH corresponds to 1 molar equivalent:

A methyl formate/potassium carbonate molar ratio of 2.0, in contrast, leads to the formation of potassium formate HCOOK, since 1 mol of $K_2CO_3$ corresponds to 2 molar equivalents:

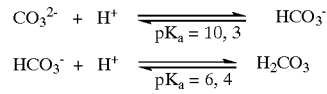

Depending on the molar ratio employed of methyl formate to the molar equivalent of the basic compound, the reaction product obtained is a mixture containing formate $HCOO$—$M^{x+}{}_{1/x}$ (without excess of formic acid) or acid formate (I) $HCOO$—$M^{x+}{}_{1/x}$*y HCOOH and methanol, if appropriate water and if appropriate reaction products of the basic compound.

The methanol formed is separated off in the inventive process from the resultant reaction mixture, in which case, if appropriate, other components, for example formic acid, can be added to this reaction mixture in advance. The methanol can be removed, for example, by the customary known processes, for example by evaporation. In the evaporation of methanol, it is also possible to separate off conjointly a portion of any water present, if appropriate all of the water. Preference is given to evaporating methanol without significant amounts of water, since in this case methanol is predominantly obtained as condensate, which can, for example, be reused in the synthesis of methyl formate by carbonylation. A further possible process for separating off the methanol formed is crystallization and removal of the formate HCOO—$M^{x+}{}_{1/x}$ or the acid formate (I) HCOO—$M^{x+}{}_{1/x}$*y HCOOH, in which a mother liquor containing methanol and formate or acid formate is obtained. By subsequent distillation, methanol can be obtained from this mother liquor. The remaining bottom phase product is advantageously recirculated to the formate synthesis stage.

If in the said reaction a product having a lower formic acid content than desired was obtained (for example formate alone, without an excess of formic acid), formic acid can be added subsequently to the mixture obtained. Generally it is advantageous in this case first to remove the methanol formed (for example by distillation) and then, by adding formic acid, to set the desired acid content of the acid formate.

If the reaction between the methyl formate, the water and the basic compound is carried out in such a manner that firstly only formate (without excess of formic acid) or formate with a very slight excess of formic acid is formed, the desired acid content of the acid formate to be prepared must be set by adding formic acid. The addition can be made, as mentioned above, before or after separating off the methanol.

Preference is given in the inventive process to the preparation of acid formates in which the methyl formate is reacted with water and a basic compound, as defined above, directly to form acid formates (I) and the methanol formed is separated off. In this preferred variant, subsequent setting of the desired acid content by subsequent addition of formic acid is generally no longer necessary.

In the inventive process, generally a molar ratio of methyl formate "n(methyl formate)" in the fresh feed to the molar equivalent of the basic compound "n' (basic compound)" in the fresh feed, taking into account all dissociation states which lead, by addition of protons, to conjugate acids which have a $pK_a$ of $\geq 3$, measured at 25° C. in aqueous solution, of $$\frac{n(\text{methyl formate})}{n'(\text{basic compound})}$$

of from 0.5 to 100 is used. Preferably, said molar ratio is from 1.0 to 10, particularly preferably from 1.1 to 20, very particularly preferably from 1.5 to 6, and in particular from 1.9 to 4.1. The term "fresh feed" is the starting material stream fed externally to the production plant for preparing the acid formates without taking into account any recirculated components.

The amount of water to be used in the inventive process can vary over a broad range. Generally, in the inventive process, in the reaction, a concentration of water of from 0.1 to 95% by weight, preferably from 5 to 80% by weight, and particularly preferably from 10 to 70% by weight, in the reaction apparatus is used.

The amount of freshly fed water generally corresponds to the amount stoichiometrically required for the reaction. The inventive process is generally carried out at a temperature of from 0 to 150° C., preferably from 30 to 120° C., and particularly preferably from 50 to 80° C. When the inventive process is carried out, the pressure is generally from 0.05 to 1 MPa absolute, preferably from 0.08 to 0.5 MPa absolute, and particularly preferably from 0.09 to 0.15 MPa absolute.

Reaction apparatuses which can be used are in principle all reaction apparatuses which are suitable for reactions in the liquid phase. Examples are stirred tanks and jet loop reactors.

The methanol formed is separated off in the inventive process preferably by evaporation from the reaction mixture. Suitable methods for evaporation are distillation and stripping. In distillation the resultant reaction mixture is generally transferred to a batchwise, semicontinuous or continuous column and distilled there. However, it is also possible to evaporate off the methanol from the reaction apparatus after the reaction. In this case the reaction apparatus is advantageously fitted with a distillation attachment. In the case of stripping, a stripping gas is passed through the reaction mixture. Suitable stripping gases are in principle all gases which are inert with respect to the reaction mixture, for example air, nitrogen, oxygen, noble gases or mixtures thereof.

If it is intended to prepare aqueous solutions of the acid formates, generally, after the methanol removal, the desired water content is set. This is achieved by supplying or distilling off water.

In a preferred embodiment of the inventive process, the mixture obtained after methanol removal is cooled for crystallization and the precipitated acid formates are separated off. Said crystallization is generally carried out at a temperature in the range from −20° C. to +30° C., and preferably from 0° C. to 30° C.

Generally, the amount of product crystallized out increases with decreasing temperature. Crystallization can in principle be carried out in all known apparatuses therefor. It can proceed, for example, following the methanol removal, directly in the reaction apparatus, in the column bottom phase, in a further stirred tank or in a crystallizer. Said embodiment can be used particularly advantageously for separating off acid formates which are crystallizable in the desired composition. Relevant examples are potassium diformate (HCOOK*HCOOH), sodium diformate (HCOONa*HCOOH), sodium tetraformate (HCOONa*3 HCOOH) or mixtures thereof.

The crystallized formates or acid formates are generally removed by conventional and known methods, for example by filtration or centrifugation.

The mother liquor obtained after separating off the acid formates is preferably reused in the reaction of methyl formate with water and the basic compound.

The reaction of methyl formate with water and the basic compound, the removal of methanol and the isolation of the acid formates can be carried out batchwise, semicontinuously or continuously. Preferably, said reaction and removal of methanol are carried out continuously.

Particularly preferably, in the inventive process potassium diformate (HCOOK*HCOOH), sodium diformate (HCOONa*HCOOH), sodium tetraformate (HCOONa*3 HCOOH) or mixtures thereof, and in particular potassium diformate are prepared.

The acid formates are generally prepared in the form of their solutions or crystalline as solids. To them may be added other components, for example other formate salts. In the case of the crystalline acid formates, it is generally advantageous for storage, transport and use to compress these together with a dessicant, for example silicates or starch, to give a particulate compactate or various shaped bodies, for example tablets or spheres.

In addition, the invention relates to the use of the inventively prepared acid formates for preserving and/or acidifying materials of plant or animal origin. Examples are the use of acid formates for preserving and acidifying grass, agricultural crops, fish and fish products and meat products, as are described, for example, in WO 97/05783, WO 99/12435, WO 00/08929 and WO 01/19207.

Furthermore, the invention relates to the use of the inventively prepared acid formates for treating biowastes. The use of acid formates for treating biowastes is described, for example, in WO 98/20911.

The invention also relates to the use of the inventively prepared acid formates as an additive in animal nutrition and/or as growth promoters for animals, for example breeding sows, fattening pigs, poultry, calves and cows. Said use is described, for example, in WO 96/35337. Preference is given to the use of the inventively prepared potassium acid formates, in particular potassium diformate, as an additive in animal nutrition and/or as growth promoters for animals, in particular for breeding sows and fattening pigs.

In addition, the invention relates to the use of the inventively prepared acid formates for preserving and/or acidifying materials of plant or animal origin, for treating biowastes and/or as an additive in animal nutrition.

Particular preference is given to the use as an additive in animal nutrition. Preferred acid formate-containing products are the mixtures below:

|  | Mixture 1 (% by weight) | Mixture 2 (% by weight) |
| --- | --- | --- |
| Potassium diformate | 20 to 60 | 60 to 99 |
| Sodium diformate/tetraformate | 20 to 50 | — |
| Calcium formate | 0 to 25 | 0 to 28 |
| Desiccant (silicate or starch) | 0 to 4 | 0 to 4 |
| Water | 0 to 5 | 0 to 5 |

Very particular preference is given to the use of the inventively prepared potassium diformate in animal nutrition in the form of a product of composition 98.0±1% by weight potassium diformate, 1.5±1% by weight silicate and 0.5±0.3% by weight water.

In a general embodiment for the continuous preparation of potassium diformate, an aqueous potassium hydroxide and/or potassium formate solution is placed in a reactor (for example a stirred tank), the solution is heated to the desired temperature of preferably from 50 to 80° C. and methyl formate introduction is started, with stirring. The amount of water present was set in such a manner that, under the reaction conditions, all of the potassium salt used and also the potassium formate formed are present in dissolved form. After an amount of 1 mol of methyl formate, based on 1 mol of potassium salt used, has been added, introduction of further potassium salt solution is started, in parallel with the feed of methyl formate. The stoichiometry between methyl formate and the potassium salt is then further 1:1. After the desired liquid level in the reactor has been achieved, transfer to a distillation column is started. There, after the operating point has been reached, methanol is distilled off overhead continuously. The resultant methanol can, for example, be reused in the synthesis of methyl formate via carbonylation. The resultant bottoms discharge is passed into a crystallization vessel, an equimolar amount, based on potassium formate, of formic acid is added with stirring, and the mixture is cooled to a temperature of from 10 to 25° C., potassium diformate precipitating out. The precipitated potassium diformate is separated off via filtration or centrifugation and fed to a drier. The mother liquor, which still contains further dissolved potassium formate and formic acid, is continuously recirculated to the reaction apparatus.

In a preferred embodiment for the continuous preparation of potassium diformate, an aqueous potassium hydroxide and/or potassium formate solution is placed in a reactor (for example a stirred tank), the solution is heated to the desired temperature of preferably from 50 to 80° C. and methyl formate introduction is started, with stirring. The amount of water present was set in such a manner that, under the reaction conditions, all of the potassium salt used and also the potassium formate formed are present in dissolved form. After an amount of 2 mol of methyl formate, based on 1 mol of potassium salt used, has been added, introduction of further potassium salt solution is started, in parallel with the feed of methyl formate. The stoichiometry between methyl formate and the potassium salt is then further 2:1. After the desired liquid level in the reactor has been achieved, transfer to a distillation column is started. There, after the operating point has been reached, methanol is distilled off overhead continuously. The resultant methanol can, for example, be reused in the synthesis of methyl formate via carbonylation. The resultant bottoms discharge is passed into a crystallization vessel and cooled to a temperature of from 10 to 25° C., potassium diformate precipitating out. The precipitated potassium diformate is separated off via filtration or centrifugation and fed to a drier. The mother liquor, which still contains further dissolved potassium formate and formic acid, is continuously recirculated to the reaction apparatus.

The inventive process makes it possible to prepare acid formates on an industrial level in high yield with simultaneously high flexibility with respect to composition and using readily accessible raw materials with a simple process design and low capital costs. In addition, the process has the decisive advantage that the formate and, in the preferred embodiment, the formic acid content also, of the acid formate can be produced directly from methyl formate without the costly and resource-consuming diversion via concentrated formic acid. The inventive process is therefore simple to carry out in processing terms and, compared with the processes involving direct use of concentrated formic acid according to the prior art, has significantly lower capital and energy costs. In addition, the use of highly alloyed steels is not necessary, since the acid formates are far less corrosive than concentrated formic acid.

EXAMPLES

Example 1

50 g (2.78 mol) of water, 10 g of potassium formate containing 2% by weight of water (equivalent to 0.12 mol of potassium formate), 5 g of potassium diformate containing 2% by weight of water (equivalent to 0.038 mol of potassium diformate) and 10 g (0.17 mol) of methyl formate were placed in a 400 ml glass autoclave equipped with a gas-introduction stirrer and the mixture was heated at 60° C. for 24 hours. The reaction solution was then cooled to room temperature to crystallize out potassium diformate. The potassium diformate which crystallized out was isolated and dried. From the content of methyl formate in the filtrate, determined quantitatively by gas chromatography, its conversion rate was calculated as 72%. The filtrate was concentrated completely by evaporation and the sedimented potassium diformate was isolated and dried. Both potassium diformate samples were then combined, weighed and analyzed for water and potassium contents. A potassium content of 30% by weight and a water content of 2% by weight were found, which corresponds to the composition of potassium diformate having a residual content of water of crystallization. Corrected by the amount of potassium formate and potassium diformate used, in total 15.5 g (0.12 mol) of potassium diformate were obtained.

Example 2

Example 2 was carried out in a similar manner to Example 1, except for the amount of potassium diformate used, which was 0.5 g (equivalent to 0.0038 mol of potassium diformate). The conversion rate of methyl formate was 72%. The mixed sample from the product which was crystallized out and obtained by evaporative concentration had a potassium content of 30% by weight and a water content of 2% by weight. Corrected by the amount of potassium formate and potassium diformate used, in total 15.5 g (0.12 mol) of potassium diformate were obtained.

Example 3

29.9 g (1.66 mol) of water, 9.3 g of potassium hydroxide (0.17 mol of potassium hydroxide) and 20 g (0.33 mol) of methyl formate were placed in a 400 ml glass autoclave equipped with a gas-introduction stirrer and heated at 60° C. for 24 hours. The reaction solution was then cooled to room temperature to crystallize out potassium diformate. The potassium diformate which crystallized out was isolated and dried. From the content of methyl formate in the filtrate which was determined quantitatively by gas chromatography, its conversion rate was calculated as 92%. The filtrate was concentrated completely by evaporation and the sedimented potassium diformate was isolated and dried. Both potassium diformate samples were then combined, weighed and analyzed for water and potassium content. A potassium content of 30% by weight and a water content of 2% by weight were found, which corresponds to the composition of potassium diformate having a residual content of water of crystallization. Corrected by the amount of potassium formate and potassium diformate used, in total 19.9 g (0.15 mol) of potassium diformate were obtained.

Example 4

50 g (0.89 mol) of potassium hydroxide and 10.25 g of water (0.57 mol) were placed in a 400 ml glass autoclave and heated to 60° C. Then, in the course of 6 hours at 60° C., 107 g (1.78 mol) of methyl formate were added. The reaction solution was cooled to room temperature and the liquid discharge was analyzed by gas chromatography. Methyl formate was no longer detected. The liquid discharge was concentrated to separate off water and methanol and the potassium diformate was isolated. The conversion rate of methyl formate was >99%, and the yield of potassium diformate was 116 g (0.89 mol). The water content in the potassium diformate was 2.0% by weight, and the potassium content was 29.8% by weight.

Example 5

74.8 g (0.89 mol) of potassium formate and 30.0 g of water (1.67 mol) were placed in a 400 ml glass autoclave and heated to 60° C. Then, in the course of 6 hours at 60° C., 53.5 g (0.89 mol) of ethyl formate were added. The reaction solution was cooled to room temperature and the liquid discharge was analyzed by gas chromatography. Methyl formate was no longer detected. The liquid discharge was concentrated to separate off water and methanol and the potassium diformate was isolated. The conversion rate of methyl formate was >99%, and the yield of potassium diformate was 116 g (0.89 mol). The water content in the potassium diformate was 2.2% by weight and the potassium content was 29.9% by weight.

Example 6

50 g (0.89 mol) of potassium hydroxide and 10.25 g of water (0.57 mol) were placed in a 400 ml glass autoclave and heated to 60° C. Then, in the course of 6 hours at 60° C., 107 g (1.78 mol) of methyl formate were added. The reaction solution was cooled to room temperature and the liquid discharge was analyzed by gas chromatography. Methyl formate was no longer detected. The methanol was separated off from the liquid discharge by distillation at atmospheric pressure. On cooling the bottom phase, 21 g of potassium diformate crystallizes out, which was isolated by filtration. The resultant potassium diformate is characterized by a low water content <2.0% by weight, without additional drying being performed. The residual potassium diformate can be isolated by separating off the water by distillation. The conversion rate of methyl formate was >99%, and the yield of potassium diformate was, in total, 116 g (0.89 mol).

We claim:

1. A process for preparing acid formates which comprises reacting methyl formate with water and a basic compound selected from the group consisting of sodium hydroxide, sodium hydrogen carbonate, sodium carbonate, sodium formate, potassium hydroxide, potassium hydrogen carbonate, potassium carbonate, potassium formate and/or ammonia, separating off the methanol formed and, optionally, setting the desired acid content by adding formic acid.

2. A process as claimed in claim 1, wherein a molar ratio of methyl formate in the fresh feed to the molar equivalent of the basic compound in the fresh feed, taking into account all dissociation states which lead, by addition of protons, to conjugate acids which have a $pK_a \geq 3$, measured at 25° C. in aqueous solution, of from 1.0 to 10 is used.

3. A process as claimed in claim 1 wherein, in the reaction, a concentration of water of from 0.1 to 95% by weight in the reaction apparatus is used.

4. A process as claimed in claim 1, wherein the reaction is carried out at a temperature of from 0 to 150° C. and at a pressure from 0.05 to 1 MPa absolute.

5. A process as claimed in claim 1, wherein the methanol formed is separated off by evaporation from the reaction mixture.

6. A process as claimed in claim 5, wherein the resultant mixture is cooled and the precipitated acid formates are separated off.

7. A process as claimed in claim 6, wherein the mother liquor obtained when the acid formates are separated off is reused in the reacton of methyl formate with water and a basic compound.

8. A process as claimed in claim 1, wherein potassium diformate, sodium diformate, sodium tetraformate or mixtures thereof are prepared.

* * * * *